(12) United States Patent
Tokas

(10) Patent No.: US 7,124,706 B2
(45) Date of Patent: Oct. 24, 2006

(54) LEPIDOPTERA HABITAT

(76) Inventor: Heather Tokas, P.O. Box 246, Wellsburg, WV (US) 26070

( * ) Notice: Subject to any disclaimer, the term of this patent is extended or adjusted under 35 U.S.C. 154(b) by 124 days.

(21) Appl. No.: 10/609,827

(22) Filed: Jun. 30, 2003

(65) Prior Publication Data

US 2004/0261724 A1 Dec. 30, 2004

(51) Int. Cl.
*A01K 5/00* (2006.01)
*A01K 39/00* (2006.01)

(52) U.S. Cl. .................... 119/51.01; 119/57.9
(58) Field of Classification Search ............ 119/51.01, 119/57.8, 459, 467, 473, 6.5, 57.9; D30/110, D30/124, 129; 211/49.1, 85.29, 85.31, 113, 211/119

See application file for complete search history.

(56) References Cited

U.S. PATENT DOCUMENTS

| | | | | |
|---|---|---|---|---|
| D69,262 | S | * | 1/1926 | Evenas et al. ............. D30/110 |
| 1,710,947 | A | * | 4/1929 | Payne ....................... D30/110 |
| 3,945,498 | A | * | 3/1976 | Lampinen .................. 211/49.1 |
| 4,148,533 | A | * | 4/1979 | Bustos et al. .............. 211/49.1 |
| 4,223,818 | A | * | 9/1980 | Johnson ..................... 211/49.1 |
| 4,329,789 | A | * | 5/1982 | Erickson .................... 211/113 |
| 4,333,574 | A | * | 6/1982 | Christy, Sr. ................ 211/49.1 |
| 4,765,491 | A | * | 8/1988 | Mueller ..................... 211/49.1 |
| 4,823,965 | A | * | 4/1989 | Hughes ...................... 211/49.1 |
| 5,002,013 | A | * | 3/1991 | Brown ........................ 119/6.5 |
| 5,203,281 | A | * | 4/1993 | Harwich .................... 119/57.9 |
| 5,269,258 | A | | 12/1993 | Brown |
| D352,574 | S | | 11/1994 | Brown |
| 5,377,617 | A | * | 1/1995 | Harwich ...................... 119/6.5 |
| 5,423,291 | A | | 6/1995 | Daugherty |
| 5,493,999 | A | | 2/1996 | Schenck |
| D368,336 | S | | 3/1996 | Brown |
| D408,947 | S | | 4/1999 | Mandell |
| 5,971,167 | A | * | 10/1999 | Finbow .................... 211/85.29 |
| 5,996,127 | A | | 12/1999 | Leslie |
| 6,067,934 | A | * | 5/2000 | Harwich ..................... 119/57.8 |
| D427,385 | S | * | 6/2000 | Wawzonek ................ D30/110 |
| D427,732 | S | * | 7/2000 | Corletta ..................... D30/124 |
| D431,330 | S | * | 9/2000 | Jones ........................ D30/124 |

FOREIGN PATENT DOCUMENTS

| JP | 2000197428 | * | 7/2000 |
|---|---|---|---|
| JP | 2001078680 | * | 3/2001 |

* cited by examiner

Primary Examiner—Teri Pham Luu
Assistant Examiner—Elizabeth Shaw
(74) Attorney, Agent, or Firm—John W. Renner; Renner, Otto, Boisselle & Sklar

(57) ABSTRACT

A frame supports a bundle of natural logs providing nooks, crannies or crevices attracting lepidoptera and like insects as a nesting site. The frame may be affixed to a wall, tree or post at an elevation and in a location for ease of viewing and examination. Two flexible rods or supports emulating antennae support shallow dishes disguised as flowers above and in front of the bundle. These may contain water and nectar, respectively. The bundle may be collected naturally and over time replaced. The habitat provides an attractive and natural setting to observe lepidoptera insects substantially year round.

14 Claims, 4 Drawing Sheets

LEPIDOPTERA HABITAT

DISCLOSURE

This invention relates as indicated to a lepidoptera habitat, and more particularly to a habitat and feeder designed to attract lepidopteran and like insects.

BACKGROUND OF THE INVENTION

Butterflies are fun to watch, observe, and even photograph. Like birding there is a growing interest in the feeding and observation of lepidopteran and like type insects. Such insects are not only interesting to watch and observe, even throughout the year and the various stages of their lives, but they are also useful, in for example, the pollinization of plants, as well as attracting other species.

Attempts have been made to attract butterflies with butterfly feeders. Examples may be seen in prior U.S. Pat. Nos. 6,067,934; 5,996,127; 5,493,999; 5,423,291; 5,377,617; 5,269,258; D 408 947; D 368 336; and D 352 574. These feeders however do not provide a year round natural habitat for Lepidoptera and like insects. They also may attract birds or other insects which would prey on Lepidoptera in their various stages. Accordingly, there is a need for a lepidoptera feeder which will also provide a natural habitat and a somewhat protected environment enabling observation throughout most of the year.

SUMMARY OF THE INVENTION

The lepidoptera habitat of the invention comprises a frame supporting bundle of natural logs arranged generally parallel and each preferably containing a layer of natural bark in various stages of natural decay or peeling. The parallel log bundle provides natural crevices, or nooks and crannies in which caterpillars will form cocoons or butterflies, moths and like lepidoptera will nest. It also provides protection from predators as well as harboring and hibernation areas. The log bundle imitates a natural nesting habitat and yet may be positioned on a tree, wall or post where it can easily be observed. The bundle in the frame has the general appearance of a large butterfly and is protected by a plastic solar heat releasing (black) cover. The frame may be wrought iron or plastic but again is preferably black to absorb the rays of the sun. The cover may extend out over the logs and its containing frame to provide enhanced weather protection and its edge may be shaped to fit the circumference of a tree for example. Mounted on two flexible rods emulating antennae extending out over the habitat are two shallow dishes which may contain water and nectar, respectively. The dishes are filled with sand or flat rock so the lepidoptera won't drown. Artificial colored petals project from the edge of each dish to imitate a large flower.

The log bundle may be provided by the user collected from a natural habitat and may be wholly or partly replaced upon deterioration.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF THE PREFERRED EMBODIMENTS

Referring now to FIGS. 1–4 there is illustrated a lepidoptera habitat in accordance with the present invention shown generally at 10. The habitat 10 includes a bundle of relatively small bark covered logs shown generally at 12 which bundle is contained in a frame shown generally at 14.

Figure 1:
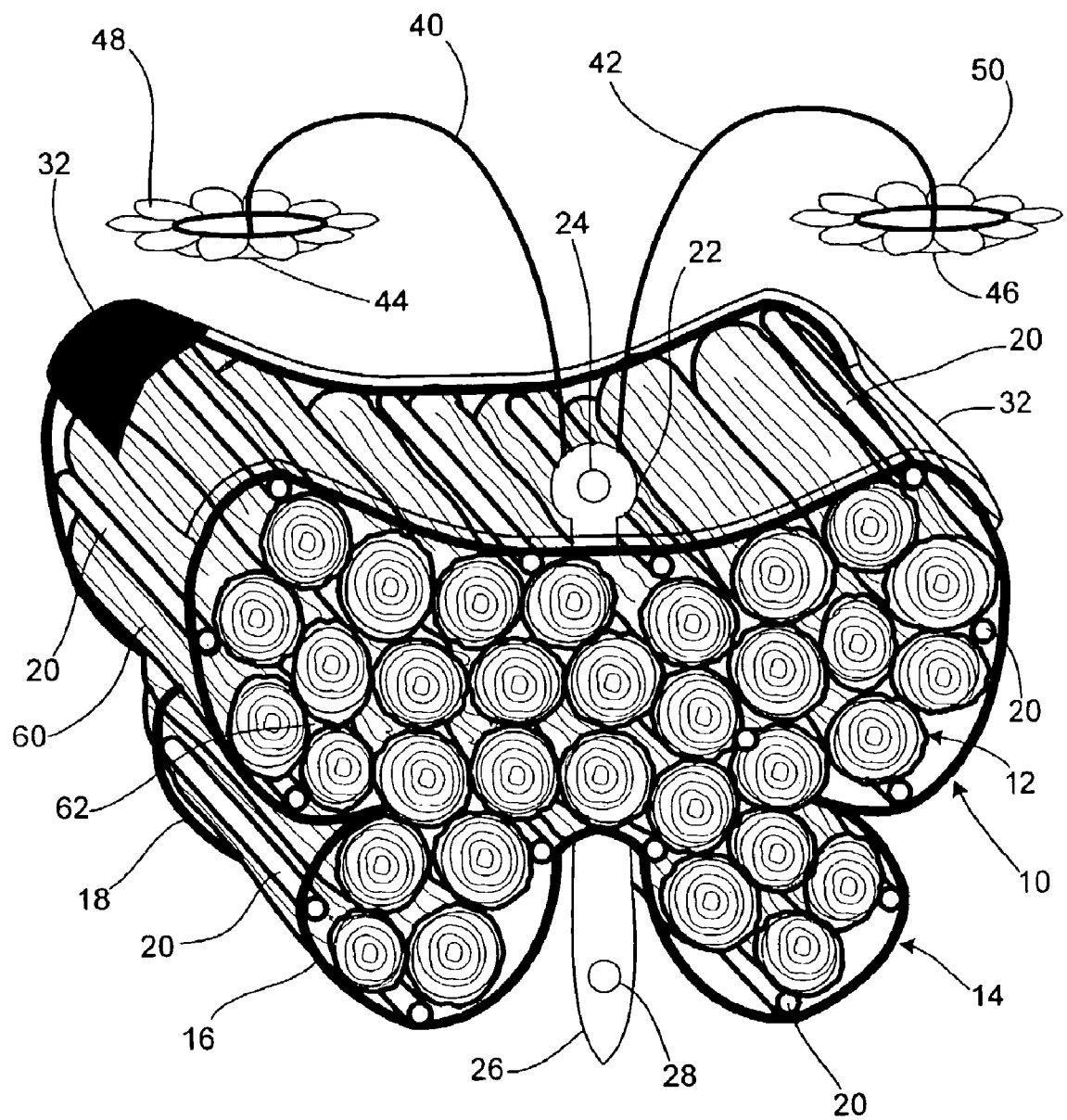
FIG. 1 is a perspective view of the lepidoptera habitat of the present invention from above and the rear, with the heat absorbing roof broken away and in phantom lines.
Figure 2:
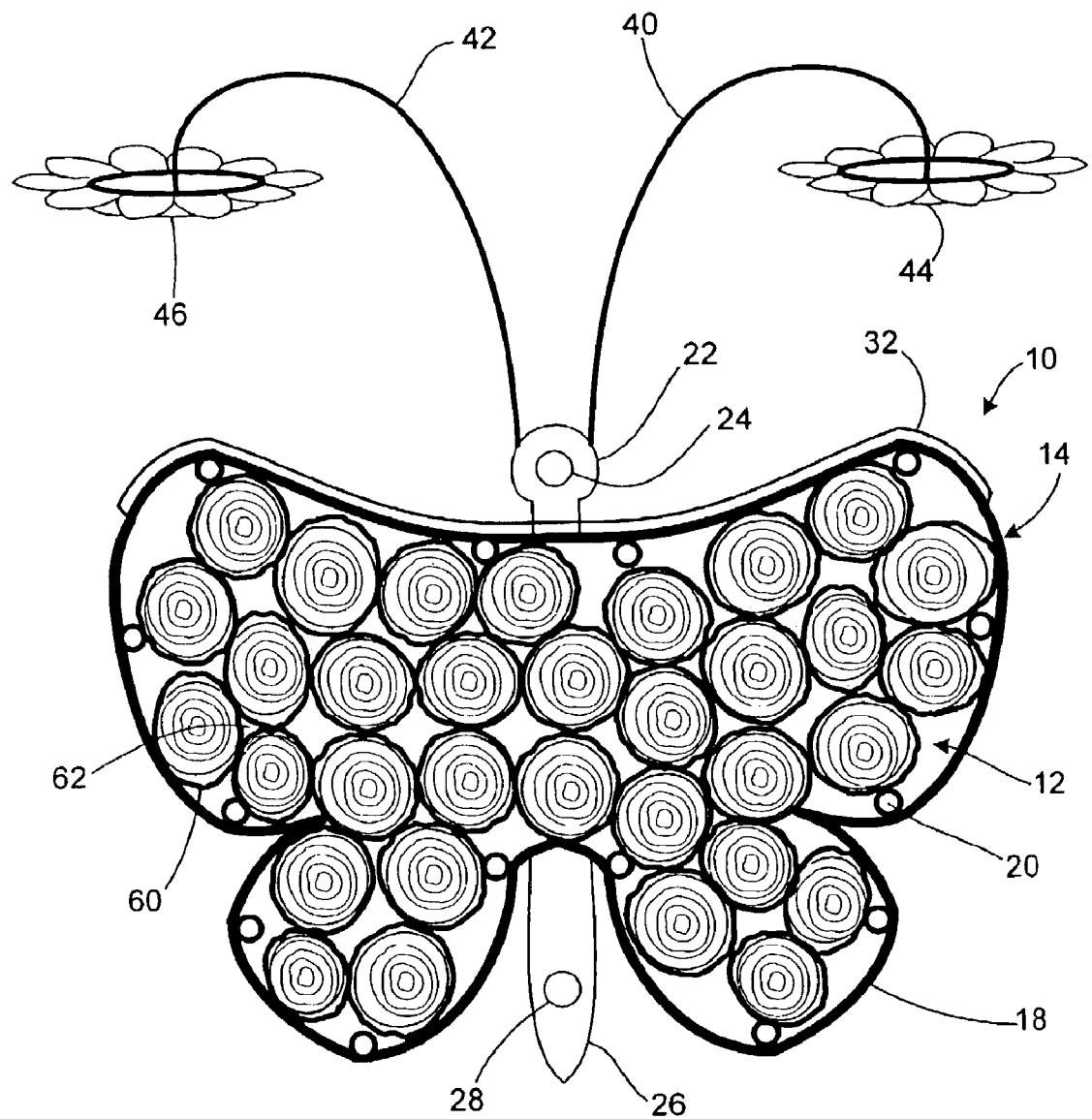
FIG. 2 is a front elevation of the habitat.
Figure 3:
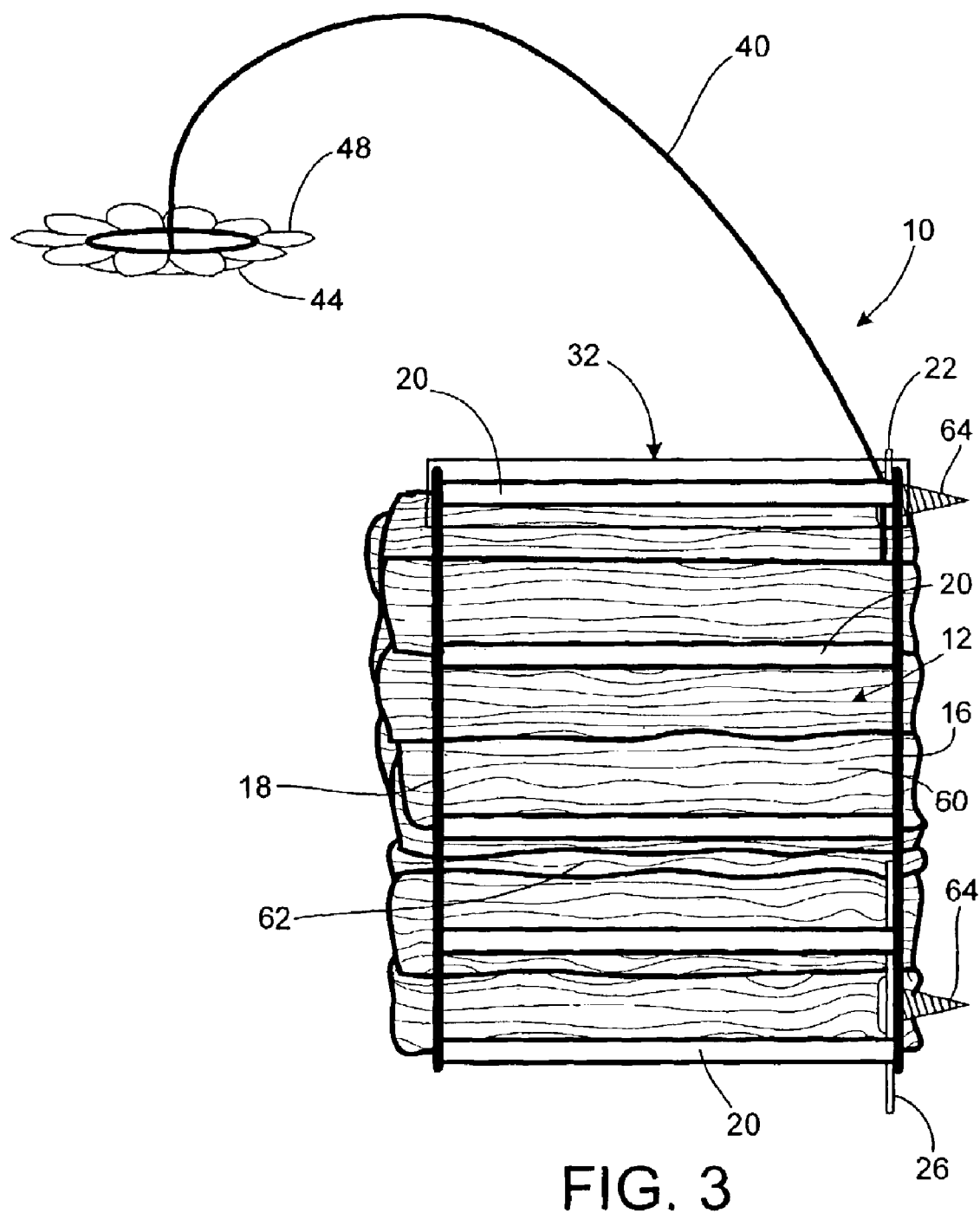
FIG. 3 is a side elevation.

As seen more clearly in FIG. 3, the frame 14 includes a rear frame 16 and a front frame 18. The front and rear frames are generally parallel and oriented in a vertical direction. The front and rear frames are connected by horizontal stringers or struts 20.

The horizontal frame members are sufficient in number and strength to space the front and rear frame members and maintain the rigidity of the frame to support the bundle of logs in elevated position.

From the center of the rear frame projects an upwardly extending top tab 22 in the general shape of a butterfly head. The tab includes a center fastener hole 24.

Also from the center of the rear frame projects a downwardly extending bottom tab 26 having a center fastener hole 28. The bottom tab is in the general shape of the tail or thorax of a butterfly.

The top of the frame is covered by a sheet or roof shown generally at 32. The sheet or roof is attached to the frame and forms a weather protective cover for the bundle of logs supported in the frame.

Figure 4:
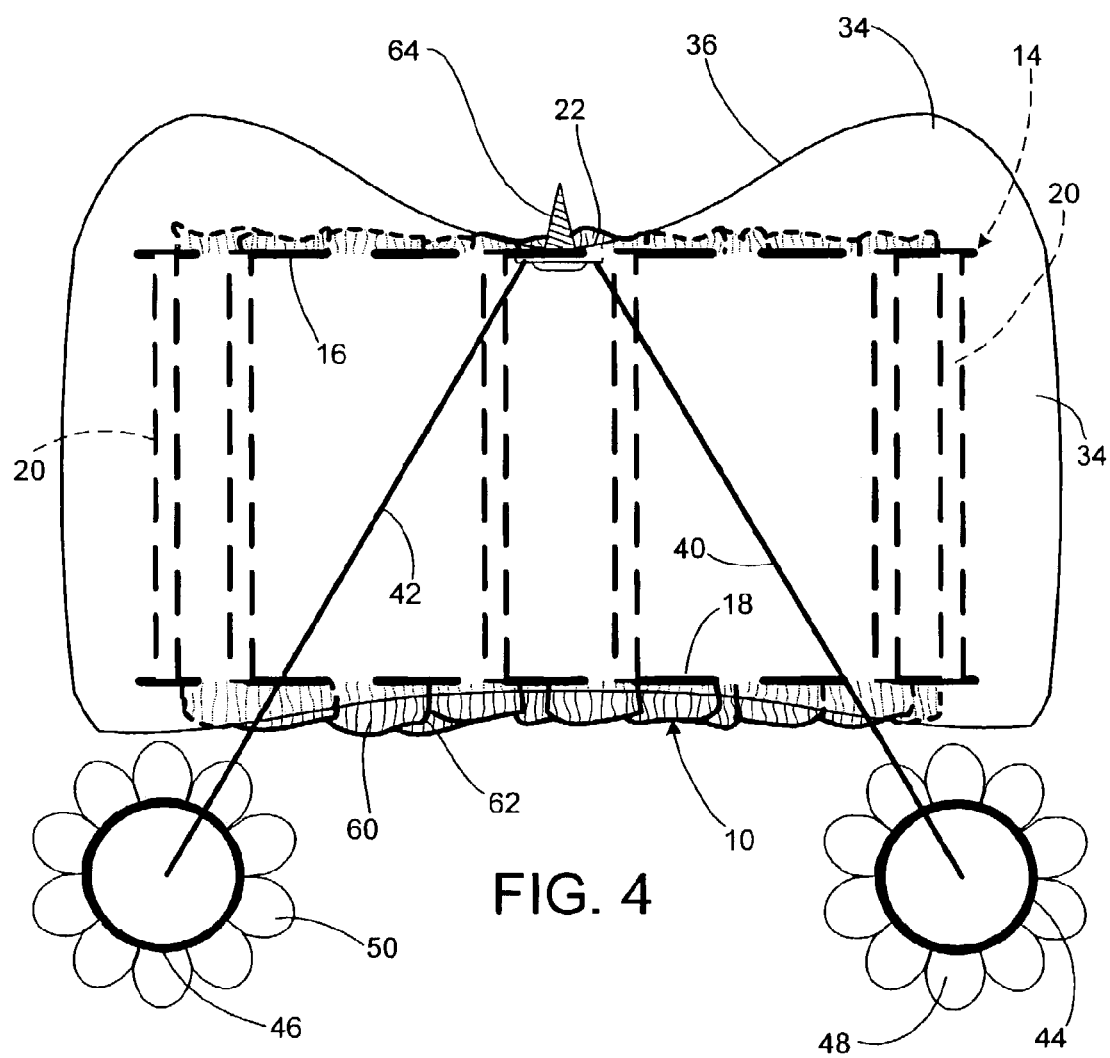
FIG. 4 is a top plan view illustrating a somewhat modified roof or top profile.

As show in FIG. 4 the roof 32 may extend beyond the frame 14 shown in dotted lines as indicated at 34 to provide additional weather protection and the edge of the roof or top 32 may be curved or scalloped as seen at 36 allowing the habitat to be mounted on a tree. In such case the roof edge may be substantially flush with the curvature of the tree trunk.

Figure 5:
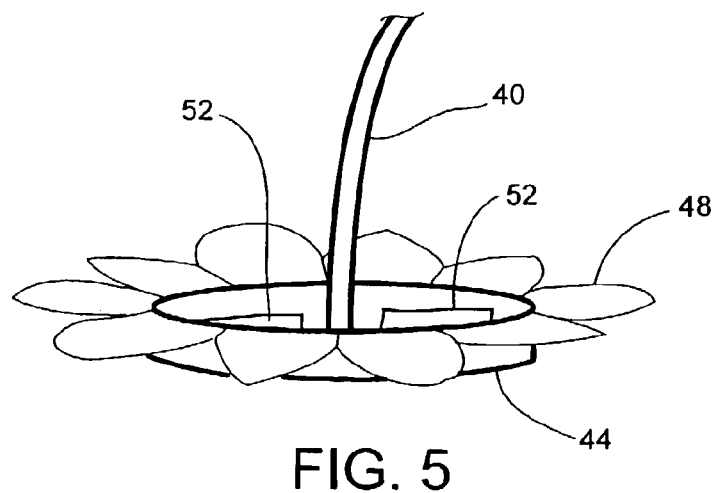
FIG. 5 is a detail of one of the water or nectar supporting artificial flowers supported by the imitation antennae.

Extending symmetrically from the top tab or projection 22 are two somewhat flexible rods 40 and 42 which extend upwardly and then forwardly and finally downwardly to support relatively shallow dishes 44 and 46. As illustrated, the rods extend symmetrically and cantilever over the span of the roof 32 so that the dishes are actually above and forward of the habitat, as seen more clearly in FIG. 5 so they won't cast significant shadows on the warming perch roof. Each shallow dish is provided at its edge or rim with projecting bright colored, preferably white, petal-like projections as seen at 48 and 50, respectively. The dishes are also preferably white.

One dish may contain water and the other nectar. Although the dishes are quite shallow it is none-the-less preferred that the dishes include solids immersed in the liquids to prevent insects from drowning. For this purpose, small flat stones or even sand may be used as shown at 52 in FIG. 5. This permits the insect literally to perch in the liquid while drinking. The rods 40 and 42 projecting from the tab 22 have the appearance of butterfly antennae. It will also be noted that the front and back frames of the habitat in elevation may have the general appearance of a butterfly with spread wings.

The frame and roof may be made from metal or plastic materials but should be black and heat absorbing in the sun. If metal, black wrought iron is preferred for the frame. The roof may be sheet metal coated black or black sheet plastic material such as a vinyl. The frame may also be formed from plastic extrusions such as tubing or other structural shapes but again, a black heat absorbing or solar type material is preferred. The frame and roof then become sun warmed perches for basking lepidoptera, which warmth is necessary in their maturation process, particularly for initial flight.

The bundle of logs 12, with the bark shown at 60 still on and in various states of decay or peeling provides a substantial number of crevices, nooks or crannies such as shown at 62 which provides protected yet ideal nesting sites for lepidoptera. Using the fastener holes in the projecting tabs the habitat can quickly be mounted at the desired viewing elevation on a tree, wall, or post for example, using the screws illustrated at 64. It should however be mounted in direct sun light. The dishes are cantilevered beyond the roof so that they will not cast a significant shadow on the roof, reducing the solar energy warming of the roof or top.

The logs may be relatively small and may be supplied separately. The width may be twenty-four inches or more and the height of the habitat may be twelve to eighteen inches or more and the logs may vary in diameter up to several inches accordingly. The shallow dishes may be about four inches in diameter and about one half inch deep. The logs in the bundle are preferably slightly longer than the distance between the front and back frames, of about the same size, and generally parallel to each other. Perfect cylindrical logs are generally not preferred, all the better to form observable nesting sites. The habitat can be viewed year round to observe the various stages of the insects and care should be taken when replacing the logs lest nesting sites are disturbed. They should not be changed in the spring, winter, or fall months.

It can now be seen that there is provided a low cost habitat and feeder for harboring, camouflaging and protecting, yet facilitating observation of lepidoptera and like insects.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. A lepidoptera habitat comprising an open frame containing a generally parallel bundle of logs to form crevices, a top on said frame comprising roof means to cover the bundle for weather protection, and tab means to hang the frame vertically elevated for convenience of viewing.

2. A habitat as set forth in claim 1 including at least one projecting feeder projecting from the top of the habitat.

3. A habitat as set forth in claim 2, wherein said feeder is in the form of a shallow dish adapted to receive nectar or water.

4. A habitat as set forth in claim 3, wherein said dish includes radial petal-like projections.

5. A habitat as set forth in claim 4, wherein said dish is supported on a flexible support positioning the dish above and in front of the habitat.

6. A habitat as set forth in claim 5 including two dishes, one for nectar and one for water, each having a flexible support.

7. A habitat as set forth in claim 6 including a solid immersed in the nectar or water to provide the lepidoptera with a solid footing at the dish.

8. A habitat as set forth in claim 1, wherein said frame includes a front frame and a back frame of the same configuration interconnected by frame members extending generally parallel to the logs of the bundle.

9. A habitat as set forth in claim 8 including tabs projecting upwardly and downwardly from the rear frame, and fastening holes in said tabs to hang the frame vertically elevated.

10. A habitat as set forth in claim 9 including flexible rods in the shape of antennae extending from said upwardly projecting tab supporting feeders above and in front of said frame.

11. A habitat as set forth in claim 10, wherein said top comprises a solar roof, the edge of which extends beyond the frame.

12. A habitat as set forth in claim 11, wherein said frame and roof are black.

13. A habitat as set forth in claim 12, wherein said habitat is in the general shape of a butterfly.

14. A method of enticing Lepidoptera comprising forming a Lepidoptera habitat by forming a bundle of short small logs, maintaining those logs as a bundle, providing a roof over the bundle to keep the bundle dry, and elevating the bundle off the ground and supporting the bundle elevated at an observable location in direct sunlight for viewing and enjoyment of Lepidoptera.

* * * * *